US009019427B2

(12) United States Patent
Laser et al.

(10) Patent No.: US 9,019,427 B2
(45) Date of Patent: Apr. 28, 2015

(54) METHOD FOR STROBOSCOPICALLY EXAMINING REPEATING PROCESSES AND ARRANGEMENT FOR PERFORMING SAID METHOD

(75) Inventors: Helmut Laser, Berlin (DE); Bjoern Thomas, Bergfelde (DE)

(73) Assignee: Xion GmbH, Berlin (DE)

( * ) Notice: Subject to any disclaimer, the term of this patent is extended or adjusted under 35 U.S.C. 154(b) by 295 days.

(21) Appl. No.: 13/518,551

(22) PCT Filed: Oct. 25, 2010

(86) PCT No.: PCT/DE2010/001246
§ 371 (c)(1),
(2), (4) Date: Jun. 22, 2012

(87) PCT Pub. No.: WO2011/076159
PCT Pub. Date: Jun. 30, 2011

(65) Prior Publication Data
US 2013/0113970 A1    May 9, 2013

(30) Foreign Application Priority Data

Dec. 22, 2009   (DE) .................. 10 2009 060 500

(51) Int. Cl.
| H04N 5/222 | (2006.01) |
| H04N 5/238 | (2006.01) |
| H04N 5/335 | (2011.01) |
| A61B 1/00 | (2006.01) |
| A61B 1/045 | (2006.01) |
| A61B 1/06 | (2006.01) |
| A61B 1/267 | (2006.01) |
| H04N 5/235 | (2006.01) |

(52) U.S. Cl.
CPC ............ *H04N 5/335* (2013.01); *A61B 1/00052* (2013.01); *A61B 1/045* (2013.01); *A61B 1/0669* (2013.01); *A61B 1/2673* (2013.01); *H04N 5/2354* (2013.01)

(58) Field of Classification Search
None
See application file for complete search history.

(56) References Cited

U.S. PATENT DOCUMENTS

| 6,120,435 A * | 9/2000 | Eino ................................ 348/65 |
| 6,734,893 B1 * | 5/2004 | Hess et al. ........................ 348/68 |
| 2002/0175992 A1 * | 11/2002 | Eino ................................ 348/65 |
| 2004/0095464 A1 * | 5/2004 | Miyagi et al. .................... 348/65 |
| 2007/0015963 A1 * | 1/2007 | Fengler et al. ................ 600/109 |
| 2007/0265504 A1 * | 11/2007 | Ott ................................ 600/199 |
| 2008/0158348 A1 * | 7/2008 | Karpen et al. ................... 348/82 |
| 2008/0183040 A1 * | 7/2008 | Abe ............................... 600/118 |
| 2008/0232130 A1 * | 9/2008 | Suda ............................... 362/574 |

FOREIGN PATENT DOCUMENTS

| DE | 699 18 460 | 8/2005 |
| DE | 10 2008 015 500 | 9/2008 |
| WO | WO-2009/008596 | 1/2009 |

* cited by examiner

*Primary Examiner* — Jason Flohre
(74) *Attorney, Agent, or Firm* — Jordan and Hamburg LLP

(57) ABSTRACT

Apparatus for examining vocal folds and a method for operating said arrangement that avoid the large fluctuations in the image brightness of the camera system and thus the flickering, which is unpleasant for the user, is provided. The apparatus comprises a stroboscopic light source, a camera control unit having a camera head, a microphone, an optical waveguide, and an optical assembly, wherein the stroboscopic light source has a signal-conducting connection to the camera control unit, and the camera head is placed on the optical assembly, wherein the camera head and the microphone have signal-conducting connections to the camera control unit, and the optical assembly is connected to the light source by means of the optical waveguide.

19 Claims, 12 Drawing Sheets

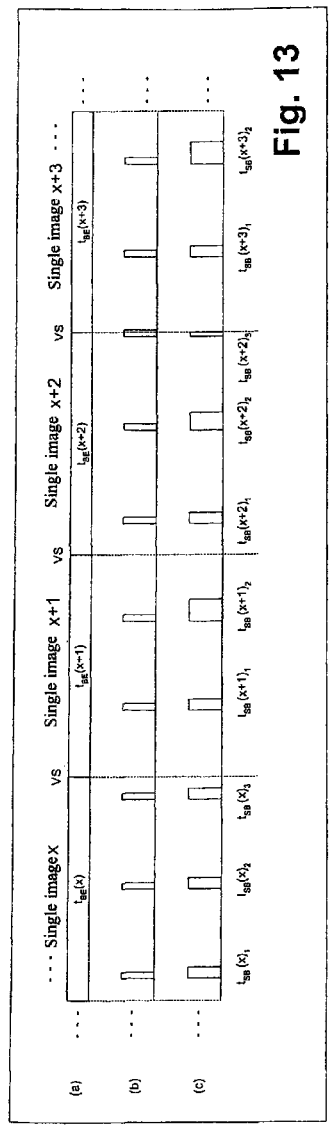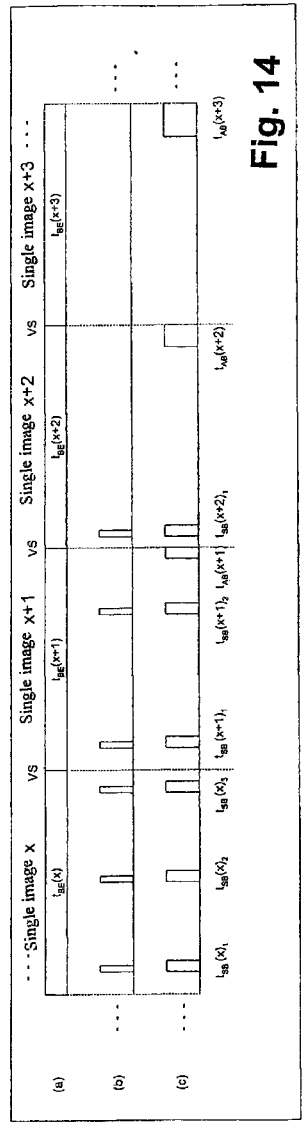

METHOD FOR STROBOSCOPICALLY EXAMINING REPEATING PROCESSES AND ARRANGEMENT FOR PERFORMING SAID METHOD

BACKGROUND OF THE INVENTION

The invention relates to a method for stroboscopically examining repeating processes, in particular for examining moving vocal folds, and to an arrangement for performing said method.

The method of stroboscopy has been known for years. Various arrangements for observing/examining periodic processes of moving vocal folds are known, too. These arrangements include illumination units based on flash lamps or LEDs in combination with a CCD or CMOS camera system.

The flash lamps or LEDs are triggered by the fundamental frequency of the voice thus producing a stationary image of the vocal folds (see FIG. 1) or, if the phases of the trigger signal are continuously shifted (0°-360°), a slowly moving image of the vocal folds (see FIG. 2).

The disadvantage of these currently available examination arrangements based on stroboscopy instruments is the missing or imperfect synchronization or control of the illuminating flashes to the camera system. This disadvantage causes fluctuations of the brightness of the camera system that are perceived by the user as an unpleasant flickering.

DE 10 2008 015 500 A1 describes a method that shall avoid the different exposure of single images by interrupting the lightning impulse during the selection phase of the image sensor (no receipt of brightness information by the image sensor) and subsequently continuing the lightning impulse. However, this method does not produce identically exposed single images and thus it does not avoid the image flickering because the constancy of the light quantity per single image is not guaranteed. Moreover, the method according to DE 10 2008 015 500 A1 is only defined for flash intervals (corresponding to the fundamental frequency of the voice) that are longer than one partial period of an image sensor. For a 50 Hz camera system, this would be equivalent to a flash frequency of less than 50 Hz. The fundamental frequency of the human voice, however, ranges between 70 and 1000 Hz.

DE 699 18 460 T2 explains a method for avoiding brightness fluctuations in the video image in which a constant exposure of the single images is ensured by a constant number of lightning impulses of constant duration per single image. This method has the disadvantage that the constant quantity of light per single image is achieved by suppressing complete lightning impulses. Said disadvantage can produce dark or considerably post-amplified and thus "noisy" video images, in particular for low fundamental voice frequencies (few lightning impulses per single image).

Furthermore, the method used in DE 699 18 460 T2 requires that the exposure control of the camera is turned off because otherwise brightness fluctuations in the video image are produced due to the exposure control of the camera. If the light quantities per single image are high, an activated exposure control of the camera will block the receipt of brightness information by the image sensor for a specific period. If one lightning impulse comes exactly in this blocked period, it will be suppressed by the camera exposure control and thus it does not contribute to the brightness of the video image. This suppression is not detected in this method and therefore it will lead to differently exposed single images if the camera is turned on and consequently to brightness fluctuations in the video image.

However, a deactivation of the exposure control of the camera has the disadvantage that the brightness of the video image is not controlled any longer. Thus, crossfades will occur in the video image if very bright objects are viewed and dark objects will be difficult to see.

Moreover, DE 699 18 460 T2 reveals a standard generator circuit that generates a signal for providing the illumination within time intervals in which a trigger signal does not exist for the lightning impulses. According to DE 699 18 460 T2, this standard generator circuit is not synchronized with the camera system. Consequently, the flashes produced by this generator circuit will cause brightness fluctuations in the video image even if the camera exposure control is turned off. The video image will flicker if a trigger signal is not provided.

SUMMARY OF THE INVENTION

The aim of this invention is to provide a method for stroboscopically examining repeating processes, particularly for examining moving vocal folds, and an arrangement for performing said method that avoids the aforementioned disadvantages of the state of the art, such as the strong fluctuations of the image brightness of the camera system and the resulting flickering which is unpleasant for the user.

The essence of the inventive method for the stroboscopic examination of repeating processes is based on an arrangement for activating an illumination unit coupled with a CCD or CMOS camera system for stroboscopically observing repeating processes, particularly moving focal folds, and said arrangement consists of an illumination unit, a CCD or CMOS camera system, an exposure control signal generator, which can be omitted if not required, a display unit, a trigger system, an electronic control unit and a driver circuit. These devices are operated by the arrangement in the following way:

The image sensor of the camera system is able to receive brightness information per single image during a defined period, ideally the maximum possible period, the lightning impulses are generated by the electronic control unit and their pulse width is varied so that the sum of the duration of the single lightning impulses is identical for each single image, and lightning impulses asynchronous to the fundamental frequency will be generated, if a trigger signal IT is not provided or is unstable.

It is advantageous if the exposure control of the camera system is active and the lightning impulses are generated by the electronic control unit in such a manner that the sum of the duration of the single lightning impulses per single image is exactly identical with the exposure time for the single image preset by the camera system.

In this method, the exposure control signal (shutter signal) of the camera system is not supplied to the image sensor and the exposure control signal (shutter signal) or another reference taken from the camera system is used as an exposure default for the exposure time per single image desired by the electronic control unit.

The essence of the arrangement for the stroboscopic examination of repeating processes is based on a stroboscopic illumination unit (flash light source), an electronic control unit, a camera system, a microphone (or EEG electrode), an optical assembly (for example an endoscope or a microscope) with optical waveguide and a display unit, and the electronic control unit, comprising a signal processing unit, a frequency meter, a default exposure time meter, a total exposure time meter, a synchronization system and a driver circuit, is coupled to the camera system via an interface.

In one embodiment, the camera head is placed on the endoscope and the camera head and the microphone have signal-conducting connections to the camera control unit, and the endoscope is connected to the light source by means of the optical waveguide.

An essential feature of the invention is the signal-conducting connection of the electronic control unit with the camera system and the illumination unit so that the lightning impulses emitted by the illumination unit are generated so that the quantity of light is identical for each single image. This identity is achieved by varying the pulse width of the lightning impulses and by generating asynchronous lightning impulses.

In one embodiment the camera system, the illumination unit (LED or flash lamp) and the control unit can be integrated and the illumination unit is connected with the endoscope by means of an optical waveguide.

In an alternative embodiment the illumination unit can be arranged separately from the control unit in an external illumination head.

Moreover, in one embodiment the illumination unit/the illuminant can be arranged in an endoscopic part of the application, the microphone can be integrated in the camera head so that the number of required connection cables to the control unit is further reduced.

The common supply line from the camera head and the connected illumination head to the camera control unit can be replaced by a wireless connection, i.e. by radio technology.

In another embodiment the illumination head can be connected to the camera head with integrated microphone so that only one cable is required for connecting all these functional groups with the control unit.

In another embodiment, the camera head, the illumination unit (illuminator) and the microphone are integrated in form of a video-endoscopic part that includes an image sensor, a microphone and the illumination unit (e.g. an LED) and is directly connected by a cable or by radio technology with a control unit or, if the endoscopic part already comprises the electronic system of the control units, directly with a display and evaluation unit.

Apart from the image sensor, microphone, illumination unit, camera electronic system and control unit, the endoscopic part can also comprise the display unit (e.g. an LCD display) and possibly a unit for data storage purposes.

The invention also allows that instead of the microphone another suitable sensor, such as an EEG (electroglottography) electrode, is used for receiving the signal for the illumination control.

BRIEF DESCRIPTION OF THE DRAWINGS

The invention will be explained in more detail by virtue of the schematic drawings of the embodiment. They show:

FIG. 13: chronological representation by using the lightning impulses generated by the inventive arrangement per single image if the trigger signal $I_T$ is stable, FIG. 14: chronological representation by using the lightning impulses generated by the inventive arrangement per single image, if the trigger signal $I_T$ is missing or instable.

DETAILED DESCRIPTION OF THE INVENTION

Figure 1:
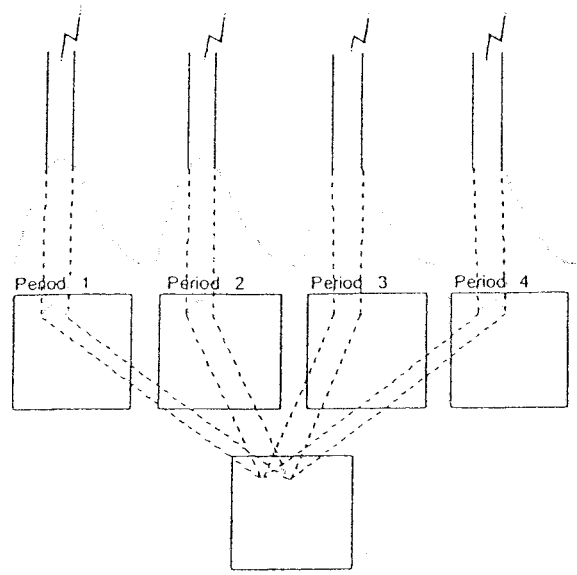
FIG. 1: a schematic drawing of the generation of a stationary image of vocal folds.
Figure 2:
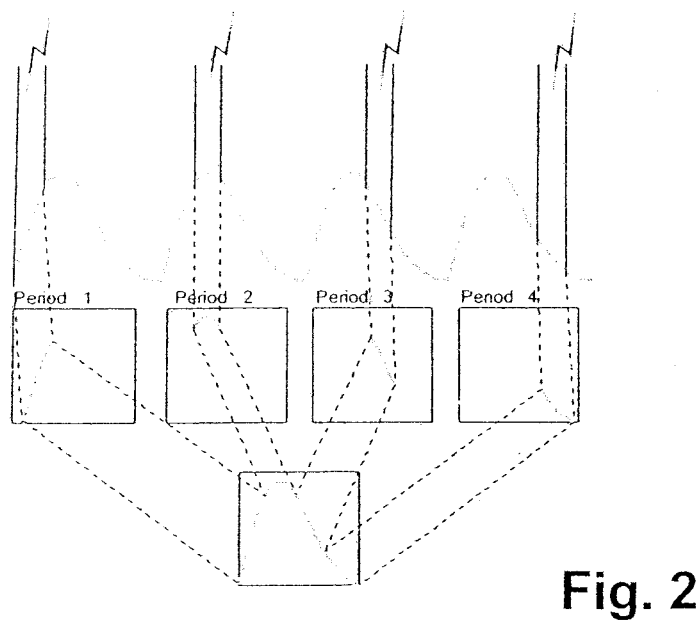
FIG. 2: a schematic drawing of the generation of a slowly moving image of vocal folds.
Figure 3:
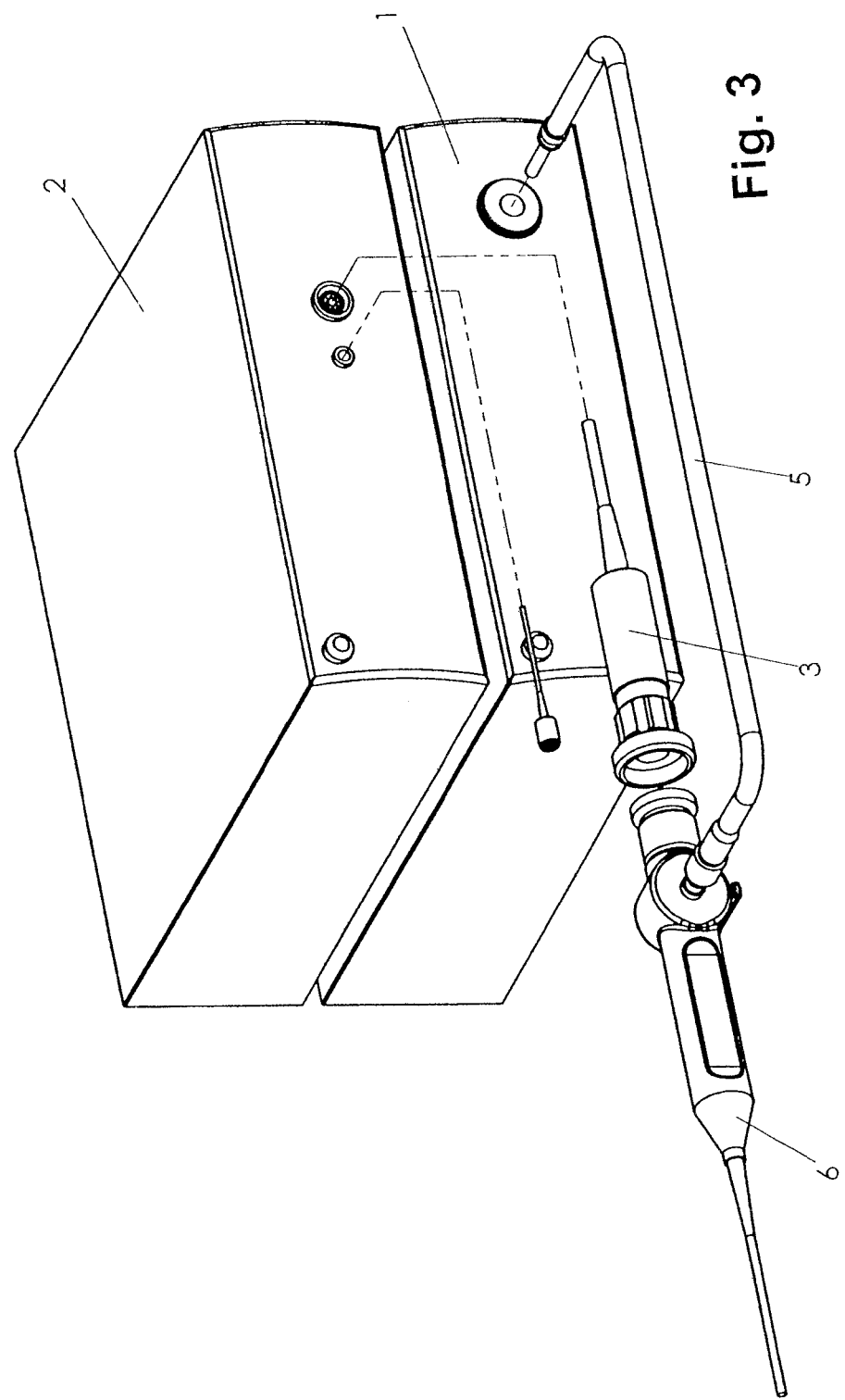
FIG. 3: a schematic drawing of a first embodiment of the inventive arrangement.

FIG. 3 shows an arrangement consisting of a stroboscopic light source (1) (comprising illumination unit and control arrangement), a control unit (2) (comprising camera control unit and control arrangement) with a camera head (3), a microphone (4), an optical waveguide (5) and an endoscope (6), and the stroboscopic light source (1) is connected with the camera control unit (2) so that the lightning impulses emitted by the illumination unit can be generated in such a way that the light quantity is identical for each single image. This identity is achieved by varying the pulse width of the lightning impulses and by generating asynchronous lightning impulses by means of the electronic control unit.

In this arrangement, the camera head (3) is placed on the endoscope (6) and the camera head (3) and the microphone (4) have signal-conducting connections and the endoscope (6) with the optical waveguide (5) is connected with the stroboscopic light source (1) (comprising illumination unit and control arrangement).

Figure 4:
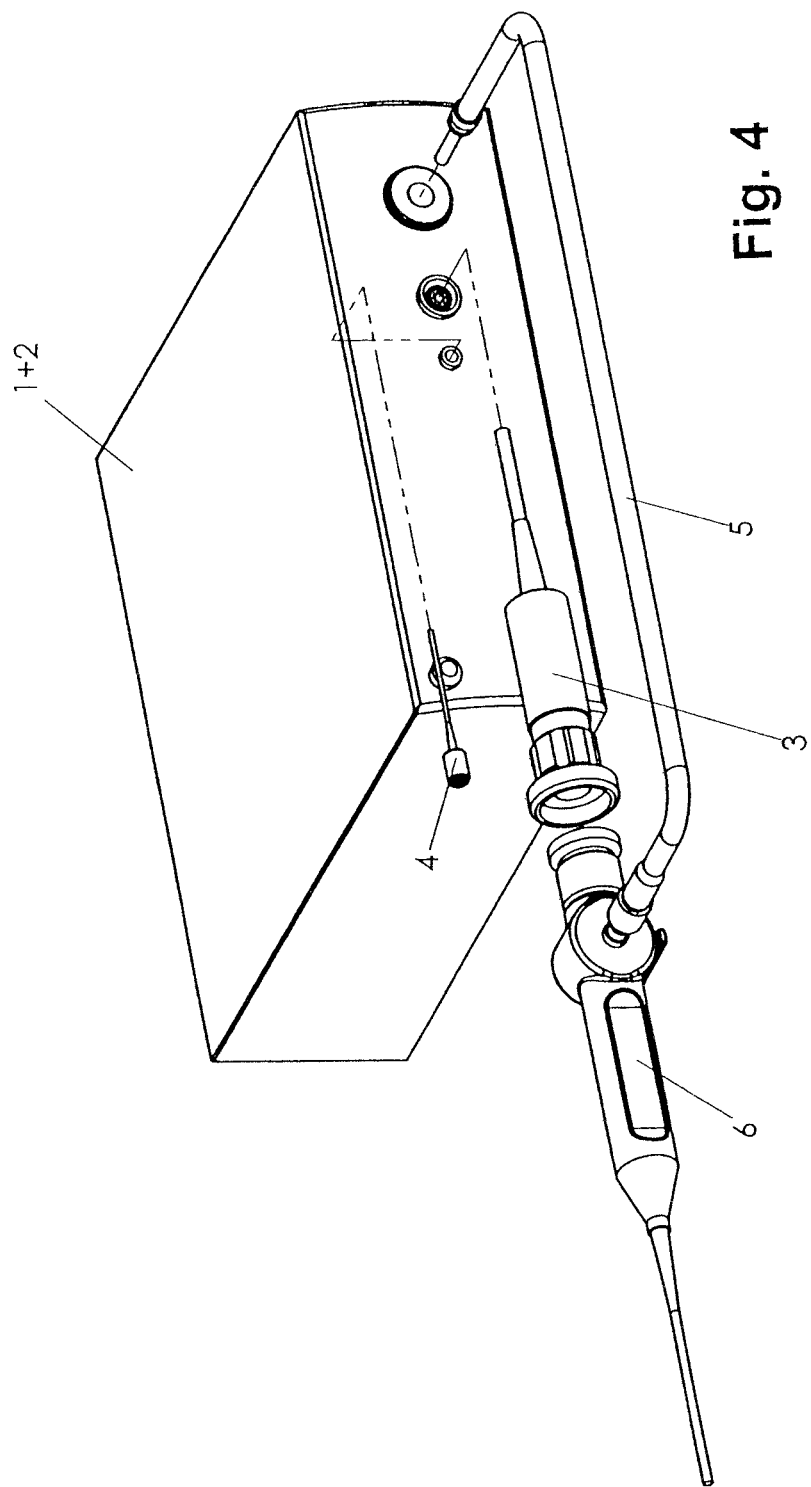
FIG. 4: a schematic drawing of a second embodiment of the inventive arrangement.

As shown in FIG. 4, it is alternatively possible that the stroboscopic light source (1) is integrated into the camera control unit (2) (1+2), the camera head (3) and the microphone (4) have signal-conducting connections to the control unit, the endoscope (6) is connected by means of the optical-waveguide (5) to the control unit (1+2), and the camera head (3) is placed on the endoscope (6).

Figure 5:
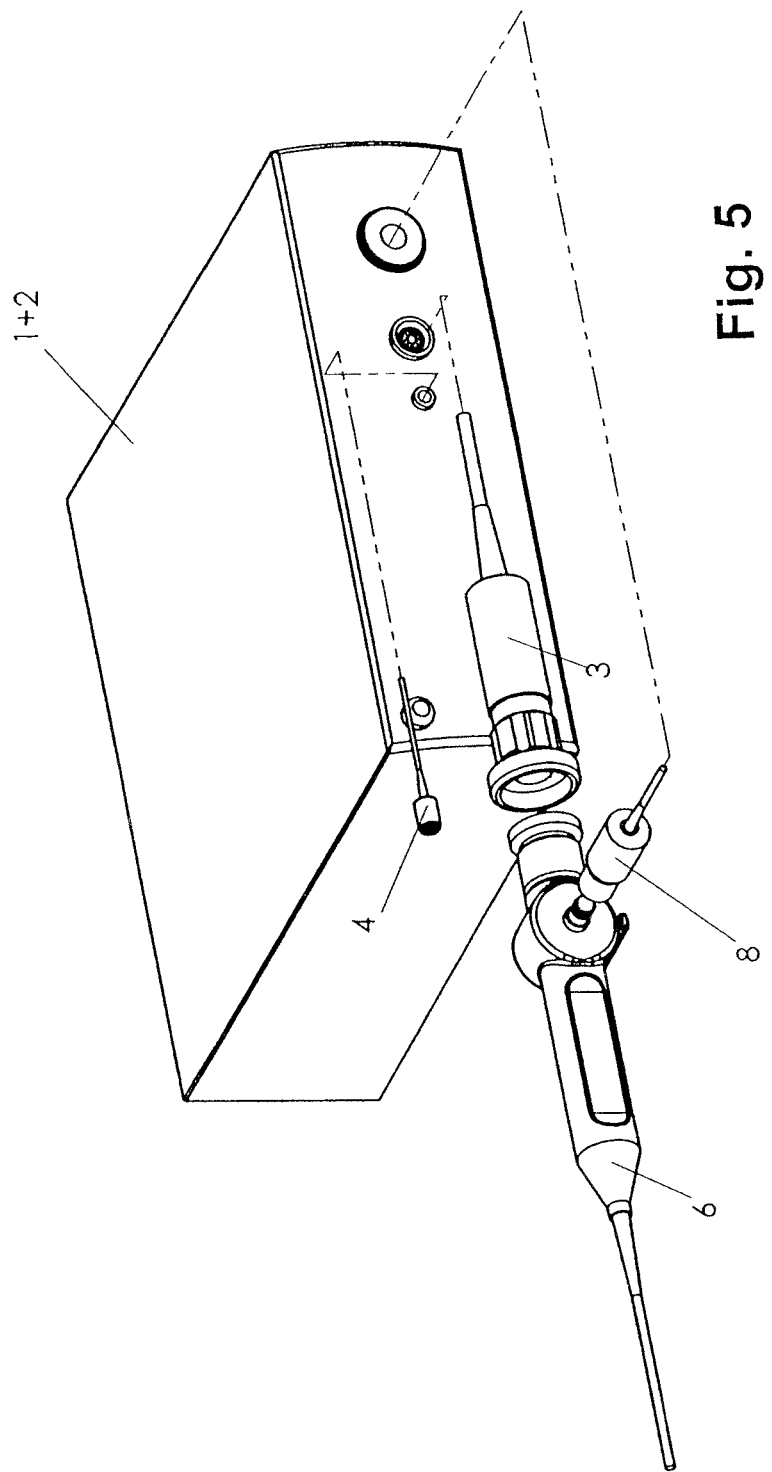
FIG. 5: a schematic drawing of a third embodiment of the inventive arrangement.

In an alternative embodiment shown in FIG. 5 the stroboscopic light source (1) can be provided with an external illumination head (8) that is separated from the control unit (2), can be connected to the endoscope (6) and has a signal-conducting connection to the control unit (2) with stroboscopic light source (1) (1+2) so that the optical waveguide is not required and only electrical connections couple the camera head (3) and the illumination head (8) and microphone (4) with the control unit (2) with stroboscopic light source (1).

Figure 6:
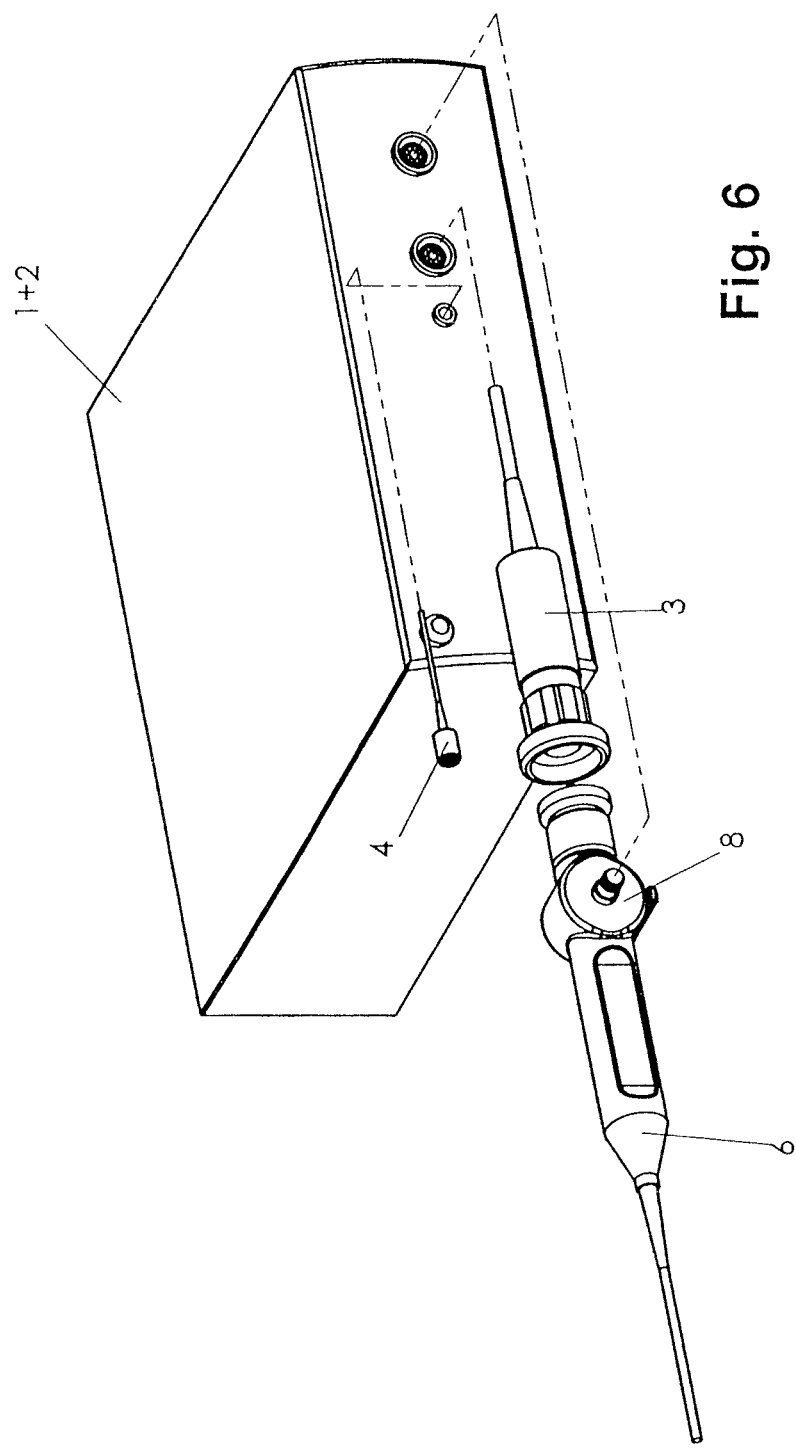
FIG. 6: a schematic drawing of a fourth embodiment of the inventive arrangement.

FIG. 6 shows that instead of an illumination head (8) the illumination unit (8) can also be directly integrated in the endoscope (6).

Figure 7:
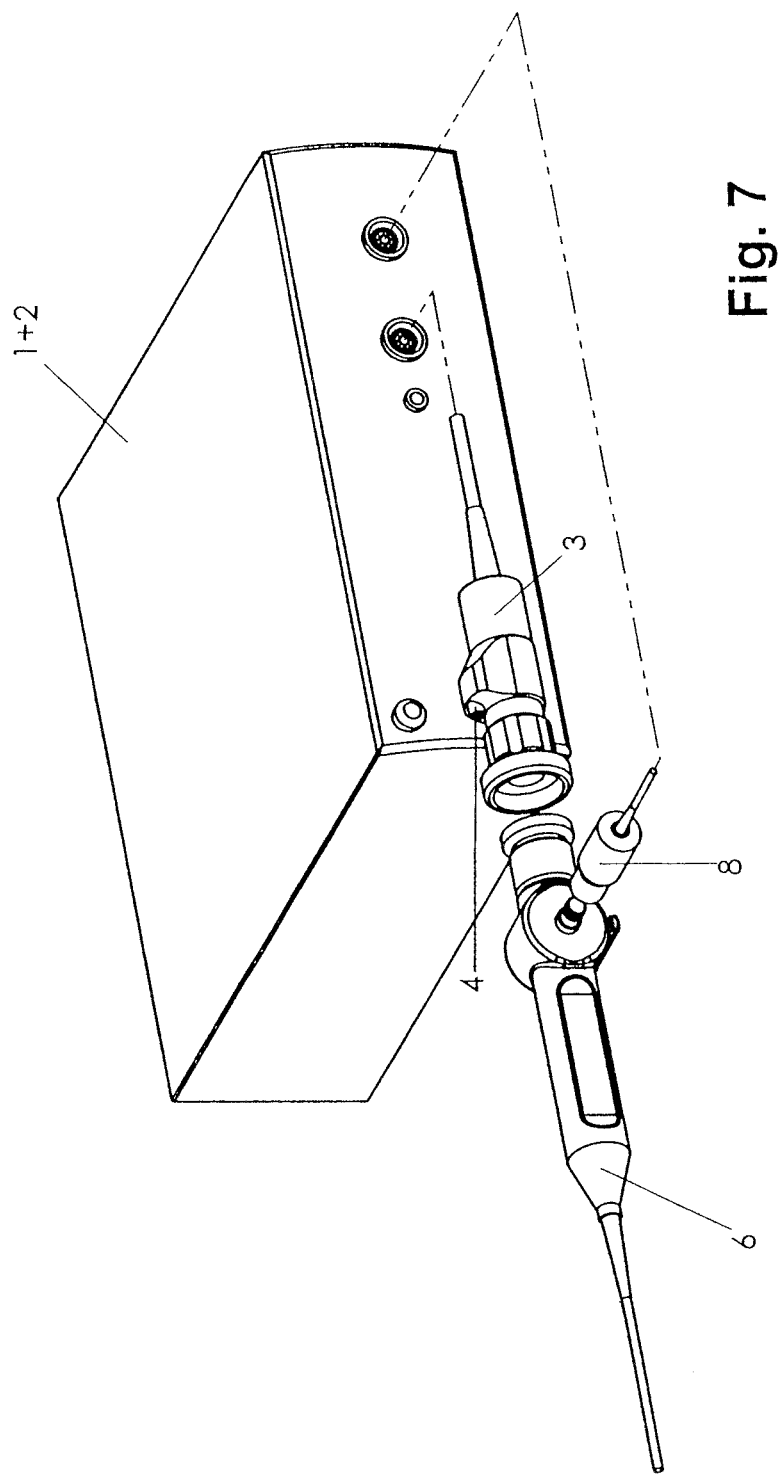
FIG. 7: a schematic drawing of a fifth embodiment of the inventive arrangement.

The invention also includes an embodiment in which the microphone (4), as shown in FIG. 7, is integrated in the camera head (3) according to FIG. 5.

Figure 8:
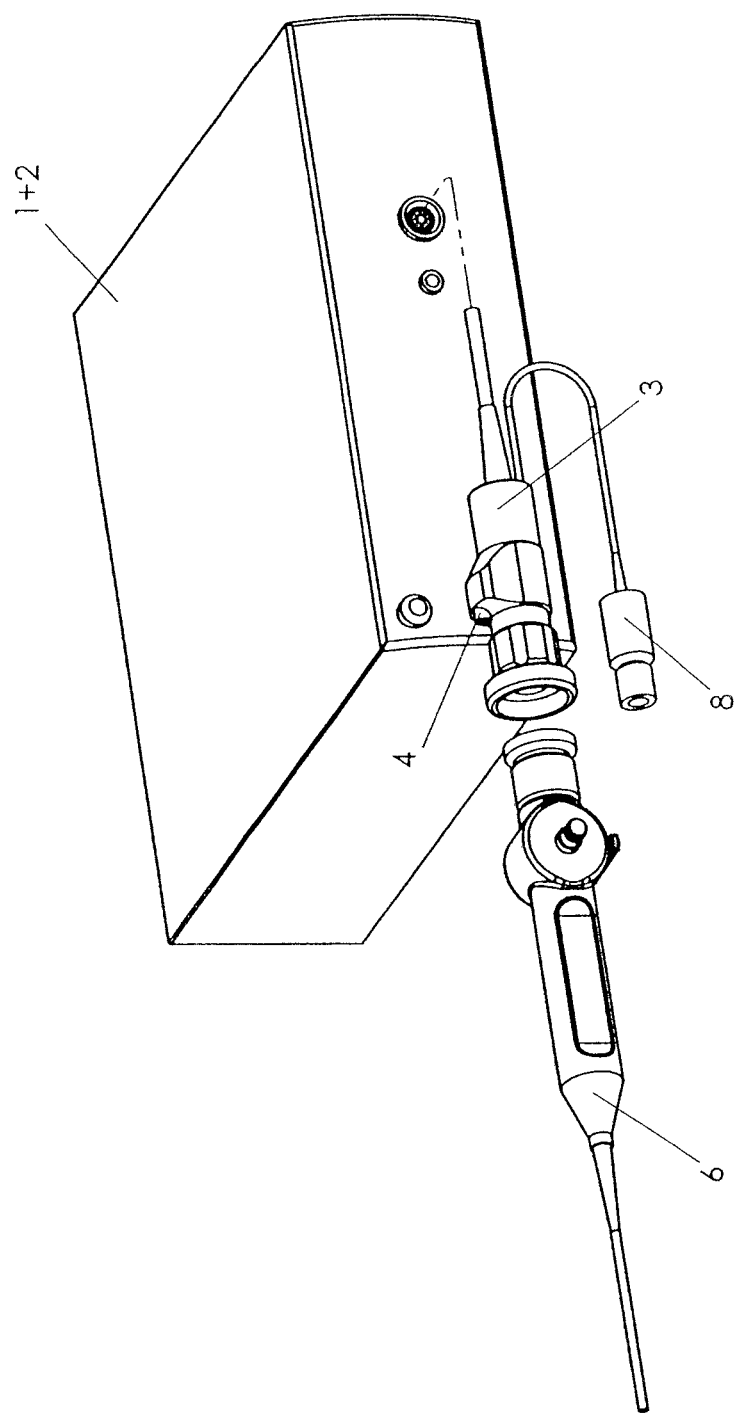
FIG. 8: a schematic drawing of a sixth embodiment of the inventive arrangement.

The invention also includes an embodiment, as shown in FIG. 8, in which the illumination head (8) is directly connected with the camera head (3) with integrated microphone (4), and a signal-conducting connection leads to the control unit (2).

Figure 9:
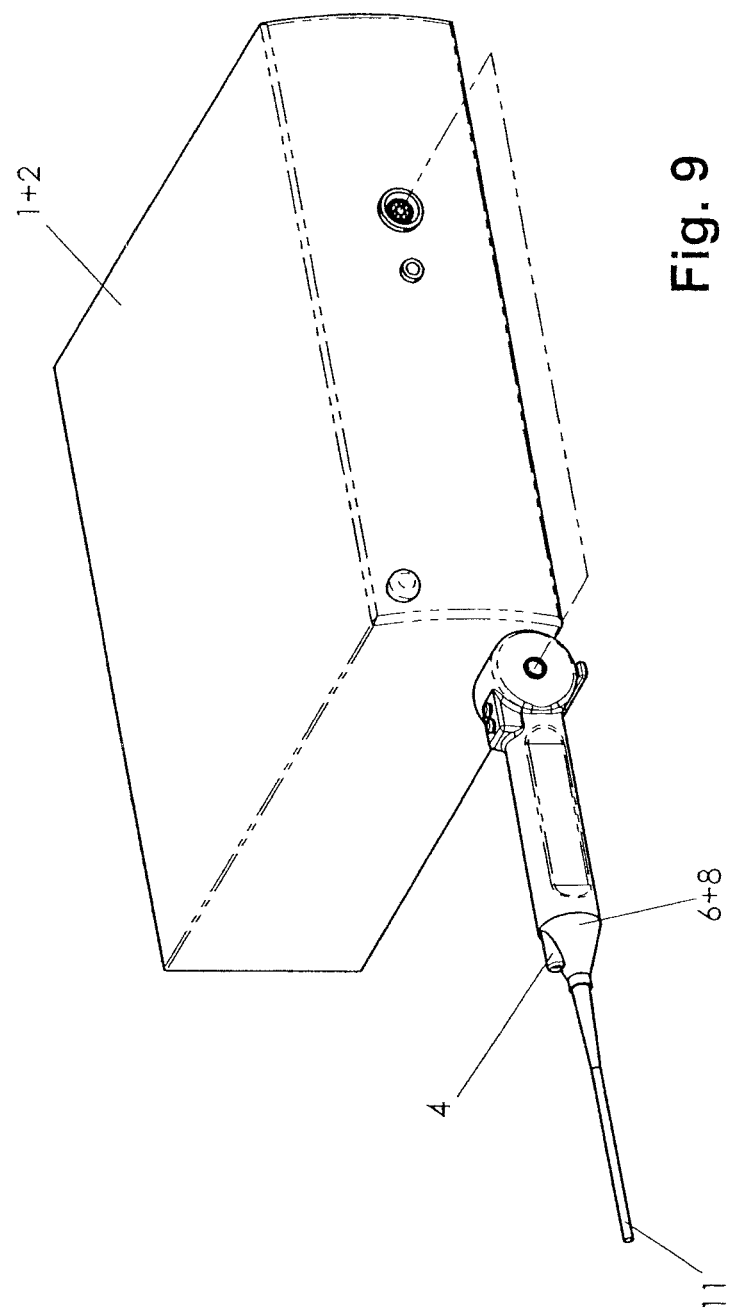
FIG. 9: a schematic drawing of a seventh embodiment of the inventive arrangement.

As shown in FIG. 9, the illumination head (8), the camera head (3) and the microphone (4) can be combined to a single endoscopic application part in the endoscope (6) so that a signal-conducting connection leads to the control unit (2).

This common connection can be replaced by a wireless connection, i.e. by radio technology.

Figure 10:
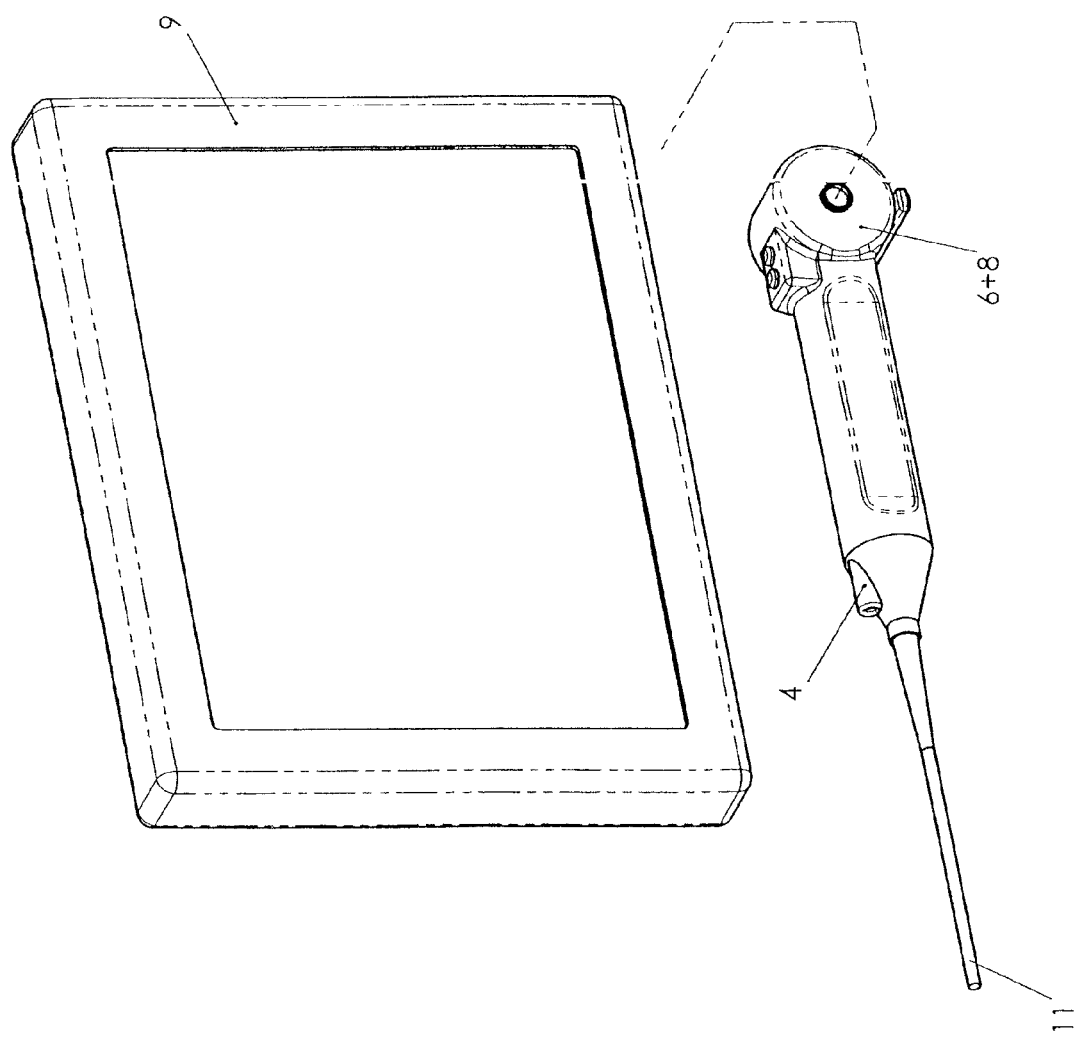
FIG. 10: a schematic drawing of the embodiment according to FIG. 9 with separate display and evaluation unit.

The endoscopic part according to FIG. 9 can be connected with a display and evaluation unit (9), as shown in FIG. 10, and apart from the image sensor (11), the microphone (4) and the illumination unit the endoscopic part also contains the camera electronic system and the control arrangement so that completed video and measurement data (e.g. fundamental frequency and sound pressure level) can be transferred to the display and evaluation unit (9) via an interface (e.g. USB or IEEE 1394).

Figure 11:
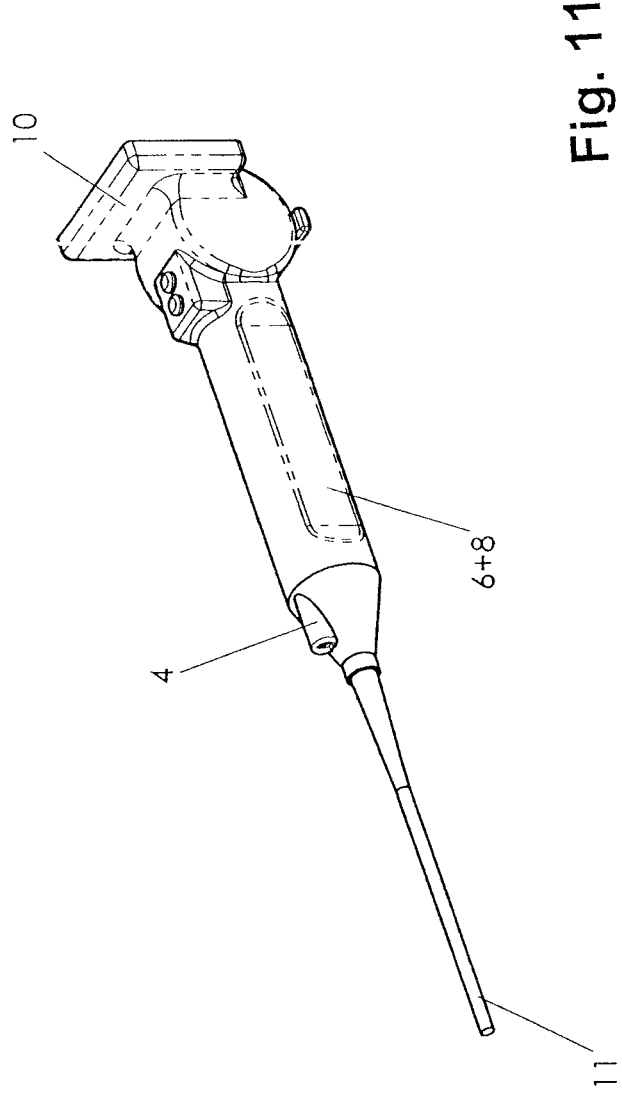
FIG. 11: a schematic drawing of the embodiment according to FIG. 9 with integrated display unit.

In an alternative embodiment, the display and evaluation unit (9) can be, for example, designed as an LCD display (10), as shown in FIG. 11, and be directly linked with the endoscope (6) by either a detachable or a permanent connection and, if required, it also contains the option of digital data recording.

It is also part of the invention that instead of the microphone another suitable sensor, such as an EEG (electroglottography) electrode, is used for obtaining the signal for the illumination control.

Figure 12:
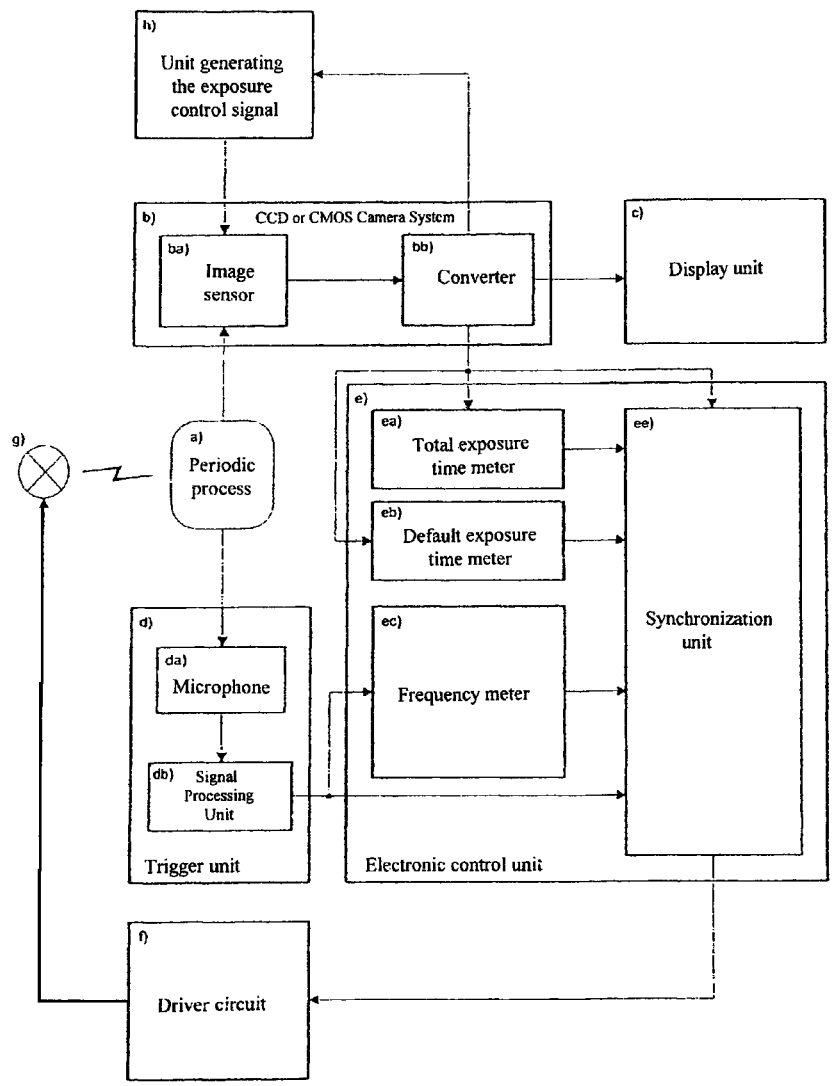
FIG. 12: block diagram of the inventive electronic control unit.

FIG. 12 contains a block diagram that shows the inventive control unit that is used for activating an illumination unit (g) coupled with a CCD or CMOS camera system (b) for the endoscopy for stroboscopically examining repeating processes (a), particularly moving vocal folds, including synchronization and control of the illuminated flashes with or to a camera system (b) for avoiding brightness fluctuations in the video image.

The inventive control unit consists of an illumination unit (g), a CCD or CMOS camera system (b), a unit for generating exposure control signals (h), which can be possibly omitted, a display unit (c), a trigger unit (d), an electronic control unit (e) and a driver circuit (f) that will be explained in the following.

The camera system (b) comprises one or more CCD or CMOS image sensors, hereinafter only referred to as image sensor, for recording the periodic process (a) illuminated by the illumination unit (g). The image sensor (ba) has a signal-conducted connection to a converter unit (bb) that uses the image information of the image sensor for generating a video signal.

The display unit (c) is, for example, a monitor for displaying the video signal provided by the camera system (b). The display unit (c) has a signal-conducting connection to the camera system (b).

The trigger unit (d) is used for generating pulses $I_T$ that are synchronous to the periodic process (a) and are transmitted to the electronic control unit (e). The trigger unit (d) consists of a microphone (da) for absorbing the acoustic waves generated by the vocal cords and of a signal processing unit (db) that has a signal-conducting connection to the microphone (da) and generates the trigger signal $I_T$.

The electronic control unit (e) has a signal-conducting connection to the camera system (b) and the trigger unit (d) and comprises the following subunits:

The total exposure time meter (ea) has a signal-conducting connection to the camera system (b) and is used for determining the maximum exposure-sensitive time per single image of the camera system (b) ($t_{BE}$). $t_{BE}$ is the maximum time per single image in which the image sensor (ba) can receive brightness information. The vertical synchronization signal (VS) of the camera system (b), which indicates the end of a single image and the start of a new one, is used for determining this time. $t_{BE}$ is determined for each VS pulse anew and transmitted to the synchronization unit (ee).

The default exposure time meter (eb) has a signal-conducting connection to the camera system (b) and is used for determining the exposure time preset by the exposure control of the camera system (b) for the single image ($t_{BV}$). The value $t_{BV}$ is limited by a maximum value $t_{BV\_max}$. The maximum value $t_{BV\_max}$ is a constant value and results from the parameters of the LED(s) of the illumination unit (g) and from the design of the illumination unit (g). It is used to exclude an electrical or thermal overload of the LED(s). The vertical synchronization signal (VS) and the illumination (shutter) signal ($SHT_{Camera}$) of the camera system (b) are used for determining $t_{BV}$. For this purpose, the duration of $SHT_{Camera}$ is calculated to determine the period in which the camera system (b) wants to allow the image sensor (ba) to receive brightness information per single image. $t_{BV}$ is determined for each VS pulse anew and transmitted to the synchronization unit (ee).

The frequency meter (ec) has a signal-conducting connection to the trigger unit (d) and the instantaneous frequency of the basic wave of the periodic process (a) is measured from the trigger pulses $I_T$ and transmitted to the synchronization unit (ee).

The synchronization unit (ee) has a signal-conducting connection to the camera system (b), the total exposure time meter (ea), the default exposure time meter (eb), the frequency meter (ec) and the trigger unit (d). The synchronization unit uses the signals provided by these systems to generate a pulse signal $I_I$ that consists of pulses $I_S$ that are synchronous to the periodic process (a) and of pulses $I_A$ that are not synchronous (asynchronous) to the periodic process (a). Both types of pulses have a variable pulse width. This pulse signal $I_I$ is transmitted to the driver circuit (f) via a signal-conducting connection.

The driver circuit (f) has a signal-conducting connection to the electronic control unit (e) and is used for triggering one or more LED(s). The driver circuit (f) ensures a constant power output per time unit to the LED(s).

Moreover, the driver circuit (f) is pulsable. That means that the point of time at which the power is output to the LED(s) can be controlled via a pulse signal. This pulse signal ($I_I$) is provided by the electronic control unit (e).

The illumination unit (g) consists of one or more LEDs that is/are electrically connected with the driver circuit (f) and used for illuminating the periodic process (a) by emitting lightning impulses.

The unit for generating the exposure control signal (h) has a signal-conducting connection to the camera system (b) and is used for generating a signal with the shutter value "0" that is conform with the exposure control signal (shutter signal) of the camera processor. That means that the image sensor is able to receive brightness information per single image during the maximally possible time. Depending on the camera system type, the unit for generating the exposure control signal is not required in some camera systems.

Advantageously, the exposure control of the camera system (b) is always active in the inventive method. However, the exposure control signal (shutter signal) is not transmitted to the image sensor (ba), as it is the case for a standard camera system, to suppress the receipt of brightness information for a specific period of time but it is used as an exposure default for the electronic control unit (e). A signal with the shutter value "0" that is conform with the shutter signal is supplied to the image sensor (ba) by the unit for generating the exposure control signal (h). That means that the image sensor is able to receive brightness information during the maximally possible period.

The control of the quantity of brightness information transferred to the image sensor (ba) and thus received by it is managed by the electronic control unit (e). In this process, the pulses $I_S$ and $I_A$ are generated by the electronic control unit (e) in such a way that the sum of the duration of the single pulses $I_S$ and $I_A$ for the single image exactly corresponds to the exposure time for the signal image ($t_{BV}$) preset by the exposure control of the camera system (b). This is achieved by adjusting the pulse widths of the pulses $I_S$ and $I_A$.

In the following, the pulses $I_S$ and $I_A$, which are generated by the synchronization unit (ee), driven by the driver circuit (f) and emitted as flashes by the illumination unit (g), are designated as lightning impulses.

If a stable trigger signal $I_T$ is provided, the electronic control unit (e) generates the lightning impulses shown in FIG. 13 (c).

The representation (a) in FIG. 13 shows the period $t_{BE}$ in which brightness information can be received per single image by the image sensor (ba). The example shows 4 successive single images.

The representation (b) in FIG. 13 shows lightning impulses that are generated synchronously to the periodic process (a) and have a constant pulse width that does not depend on $t_{BV}$. It can be seen that the light quantity provided by the lightning impulses is different in each of the 4 single images. This difference leads to differently exposed single images and thus to brightness fluctuations in the video image. The procedure described in DE 699 18 460 T2 would suppress these brightness differences by always suppressing the last lightning impulse. This method can cause the aforementioned disadvantages of dark or post-amplified and thus noisy video images.

The representation (c) in FIG. 13 shows the lightning impulses generated synchronously to the periodic process (a) by the electronic control unit (e) of this invention. The pulse width $t_{SB}$ of the lightning impulses is selected by the electronic control unit (e) so that the sum of the pulse widths per single image exactly corresponds to the exposure time for the single image ($t_{BV}$) preset by the exposure control unit of the camera system (b). If it is, for example, assumed that the camera system (b) presets the same exposure time for all 4 successive single images $$(t_{BV}(x)=t_{BV}(x+1)=t_{BV}(x+2)=t_{BV}(x+3))$$

the following will apply:

$$t_{SB}(x)_1+t_{SB}(x)_2+t_{SB}(x)_3=t_{SB}(x+1)_1+t_{SB}(x+1)_2= t_{SB}(x+2)_1+t_{SB}(x+2)_2+t_{SB}(x+2)_3=t_{SB}(x+3)_1+ t_{SB}(x+3)_2$$

The input light quantity per single image is consequently identical so that all single images are equally exposed and the video image does not contain brightness fluctuations. Moreover, synchronous lightning pulses are not suppressed completely in this method so that the probability of dark or post-amplified video images is reduced. In single image x the electronic control unit (e) generates three lightning impulses of the same pulse width. For them applies:

$$t_{SB}(x)_1+t_{SB}(x)_2+t_{SB}(x)_3=t_{Bv}(x)$$

In single image x+1 only two lightning impulses are generated in the exposure-sensitive time of the single image $t_{BE}(x+1)$. This is detected by the electronic control unit (e) and the pulse width of the last synchronous lightning impulse is prolonged (doubled in the example) to achieve the total exposure time demanded by the exposure control of the camera system (b). Thus, the following applies:

$$t_{SB}(x+1)_1+t_{SB}(x+1)_2=t_{BV}(x+1)$$

In single image x+2 two lightning impulses come with their complete pulse width into the exposure-sensitive time of the single image $t_{BE}(x+2)$. The third synchronous lightning impulse does not come with its total required pulse width into the exposure-sensitive time of the single image $t_{SB}(x+2)$. This is detected by the electronic control unit (e) and the previous synchronous lightning impulse is prolonged by the time required to achieve the total exposure time demanded by the exposure control of the camera system (b). Thus, the following applies:

$$t_{SB}(x+2)_1+t_{SB}(x+2)_2+t_{SB}(x+2)_3=t_{BV}(x+2)$$

If no trigger signal $I_T$ or an instable trigger signal $I_T$ is provided, the electronic control unit (e) will generate the lightning impulses shown in FIG. 14.

Representation (a) in FIG. 14 shows the period $t_{BE}$ in which brightness information can be received by the image sensor (ba) per single image. The example shows 4 successive single images.

Representation (b) in FIG. 14 shows the lightning impulses that are preset by the trigger signal $I_T$ and have a constant pulse width independent of $t_{BV}$. It can be seen that the light quantity provided by the lightning impulses is different in each of the 4 single images. In the fourth single image the light quantity is even zero. These different light quantities lead to differently exposed single images and thus to brightness fluctuations in the video image. The method described in DE 699 18 460 T2 would provide a trigger signal for the lightning impulses by means of a standard generator circuit. According to DE 699 18 460 T2, this standard generator circuit is not synchronized with the camera system. Consequently, the lightning impulses generated by the generator circuit cause brightness fluctuations in the video image, too.

Representation (c) in FIG. 14 shows the lightning impulses generated synchronously and asynchronously to the periodic process (a) by the electronic control unit (e) of this invention. The pulse width $t_{SB}$ and $t_{AB}$ of the lightning impulses are selected by the electronic control unit (e) in such a way that the sum of the pulse widths of the single lightning impulses per single image exactly corresponds to the exposure time ($t_{BV}$) preset for the single image by the exposure control of the camera system (b). If it is, for example, assumed that the camera system (b) presets the same exposure time for all 4 successive single images $$(t_{BV}(x)=t_{BV}(x+1)=t_{BV}(x+2)=t_{BV}(x+3))$$

the following will apply:

$$t_{SB}(x)_1+t_{SB}(x)_2+t_{SB}(x)_3=t_{SB}(x+1)_1+t_{SB}(x+1)_2+ t_{AB}(x+1)=t_{SB}(x+2)_1+t_{AB}(x+2)=t_{AB}(x+3)$$

The input light quantity is consequently identical for each single image so that all single images are equally exposed and the video image does not show brightness fluctuations. An asynchronous lightning impulse will always be generated if the still remaining exposure-sensitive time for the current single image corresponds to the still required remaining exposure time for the current single image. Then, a lightning impulse will be generated that is active until the end of the period $t_{BE}$ in which brightness information can be received by the image sensor (ba) per single image. Thus, it is ensured that no single image has a shorter exposure time in the sum than the other images even if a trigger signal $I_T$ is not supplied. In this method a video image without brightness fluctuations will also be obtained if a trigger signal $I_T$ is not available or if it is instable. Therefore, this invention guarantees video images without brightness fluctuations for a stable, an instable and a non-existing trigger signal $I_T$. Moreover, synchronous lightning impulses are not suppressed completely in this invention so that the probability of dark or post-amplified video images is reduced. Furthermore, the camera exposure control is advantageously active according to this invention and thus the brightness of the video image is always optimally controlled.

All features explained in the description, the embodiments and the following claims can be important for the invention both as a single feature and in any combination.

The invention claimed is:

1. Method for stroboscopically examining a repeating process with apparatus comprising an arrangement for triggering an illumination unit coupled with a CCD or CMOS video camera system, said arrangement operating a display unit, a trigger unit, an electronic control unit and a driver circuit, the method comprising:
   receiving at an image sensor of the camera system brightness information per single image during a defined period,
   generating lightning impulses by the electronic control for each single image wherein pulse width thereof is varied so that a sum of duration of single lightning impulses is identical for each single image, and
   generating lightning impulses asynchronous to a fundamental frequency of the repeating process when a trigger signal is not applied or is unstable.

2. Method for stroboscopically examining a repeating process according to claim 1, wherein when exposure control of the camera system is active, the sum of the duration of the single lightning impulses per single image is exactly identical with exposure time preset for the single image by the camera system.

3. Method for stroboscopically examining a repeating process according to claim 2, wherein the exposure control or shutter signal of the camera system is not transmitted to the image sensor and the exposure control or shutter signal or another reference taken from the camera system is used as an exposure default for the exposure time per single image set by the electronic control unit.

4. Method for stroboscopically examining a repeating process according to claim 1, wherein a single synchronous or asynchronous lightning impulse is composed of a series of several shorter lightning impulses the sum of which corresponds to said variable pulse width of a synchronous or asynchronous single lightning impulse.

5. Apparatus configured to stroboscopically examine a repeating process, comprising:
   an arrangement triggering an illumination unit coupled with a CCD or CMOS video camera system, said arrangement operating a display unit, a trigger unit, an electronic control unit and a driver circuit, the arrangement comprising:
   a stroboscopic light source;
   a camera control unit with a camera head;
   a microphone, an optical waveguide; and
   an optical assembly;
   wherein the stroboscopic light source is configured to have a signal-conducting connection to the camera control unit, the camera head is situated on the optical assembly, the camera head and the microphone have a signal-conducting connection to the camera control unit, and the optical assembly is connected with the light source via the optical waveguide;
   wherein an image sensor of the camera system receives brightness information per single image during a defined period,
   wherein lightning impulses are generated by the electronic control unit and pulse width thereof is varied so that a sum of duration of single lightning impulse is identical for each single image, and
   wherein lightning impulses asynchronous to a fundamental frequency of the repeating process are generated when a trigger signal is not applied or is unstable.

6. Apparatus according to claim 5, wherein the repeating process is movement of vocal folds, and the stroboscopic light source is integrated in the camera control unit, and the optical assembly is in form of an endoscope and is connected to the camera control unit via the optical waveguide.

7. Apparatus according to claim 6, wherein the stroboscopic light source is provided with an external illumination head that is separated from the camera control unit and is arranged between the endoscope and the camera head, and the illumination head has a signal-conducting connection to the camera control unit.

8. Apparatus according to claim 7, wherein the illumination head is integrated into the endoscope.

9. Apparatus according to claim 5, wherein the repeating process is movement of vocal folds, and the microphone is integrated into the camera head.

10. Apparatus according to claim 9, wherein the illumination unit is electrically connected with the camera head and a signal-conducting connection leads from the camera control unit to the camera head.

11. Apparatus according to claim 10, wherein the illumination head, the camera head and the microphone are combined to form a single part of an endoscope to which the signal-conducting connection leads from the camera control unit.

12. Apparatus according to claim 10, wherein the image sensor, the microphone, the illumination unit, electronic system of the camera and flash control are combined to form a single part of an endoscope, and the endoscope part is connectable to a display and evaluation unit via a USB or IEEE interface so that completed video and measurement data can be transferred to the display and evaluation unit.

13. Apparatus according to claim 12, wherein the display and evaluation unit comprises an LCD display.

14. Method according to claim 1, wherein the repeating process is movement of vocal folds.

15. A method for stroboscopically examining a repeating process with apparatus comprising an arrangement for triggering an illumination unit coupled with a CCD or CMOS video camera system, said arrangement operating a display unit, a trigger unit, an electronic control unit and a driver circuit, the method comprising:
   receiving at an image sensor of the camera system brightness information per single image during a defined period, wherein the image sensor senses multiple single images;
   generating one or more lightning impulses by the electronic control unit to achieve each one single image among said multiple single images, and varying for at least one single image among said multiple single images a pulse width among a plurality of said one or more lightning impulses so that for each single image among said multiple single images a sum of duration of single lightning impulses for said single image is identical, and generating lightning impulses asynchronous to a fundamental frequency of the repeating process when a trigger signal is not applied or is unstable.

16. The method for stroboscopically examining a repeating process according to claim 15, wherein when exposure control of the camera system is active, the sum of the duration of the single lightning impulses per said each one single image among said multiple single images is exactly identical with exposure time preset for said one single image by the camera system.

17. The method for stroboscopically examining a repeating process according to claim 16, wherein the exposure control or shutter signal of the camera system is not transmitted to the image sensor and the exposure control or shutter signal or another reference taken from the camera system is used as an exposure default for the exposure time per said each one single image among said multiple single images set by the electronic control unit.

18. The method for stroboscopically examining a repeating process according to claim 15, wherein each one of said one or more lightning impulses generated to achieve said each one single image among said multiple single images is a single synchronous or asynchronous lightning impulse composed of a series of several shorter lightning impulses the sum of which corresponds to said variable pulse width.

19. An apparatus configured to stroboscopically examine a repeating process, comprising:
an arrangement triggering an illumination unit coupled with a CCD or CMOS video camera system, said arrangement operating a display unit, a trigger unit, an electronic control unit and a driver circuit, the arrangement comprising:
a stroboscopic light source;
a camera control unit with a camera head;
a microphone, an optical waveguide; and
an optical assembly; and
wherein the stroboscopic light source is configured to have a signal-conducting connection to the camera control unit, the camera head is situated on the optical assembly, the camera head and the microphone have a signal-conducting connection to the camera control unit, and the optical assembly is connected with the light source via the optical waveguide;
wherein an image sensor of the camera system receives brightness information per single image during a defined period, wherein multiple single images are sensed;
wherein the electronic control unit is configured to generate one or more lightning impulses to achieve each one single image among said multiple single images, and the electronic control unit is further configured to vary pulse width of a plurality of said one or more lightning impulses for at least one single image among said multiple single images, so that for each single image among said multiple single images a sum of duration of single lightning impulse for said single image is identical; and
wherein lightning impulses asynchronous to a fundamental frequency of the repeating process are generated when a trigger signal is not applied or is unstable.

* * * * *